(12) United States Patent
Laing

(10) Patent No.: US 10,494,327 B2
(45) Date of Patent: Dec. 3, 2019

(54) CONTROLLED RELEASE PHARMACEUTICAL FORMULATIONS

(71) Applicant: United Therapeutics Corporation, Silver Spring, MD (US)

(72) Inventor: Peter Laing, Cambridge (GB)

(73) Assignee: United Therapeutics Corporation, Siver Spring, MD (US)

( * ) Notice: Subject to any disclaimer, the term of this patent is extended or adjusted under 35 U.S.C. 154(b) by 3 days.

(21) Appl. No.: 15/698,852

(22) Filed: Sep. 8, 2017

(65) Prior Publication Data

US 2017/0369416 A1 Dec. 28, 2017

Related U.S. Application Data

(62) Division of application No. 14/264,392, filed on Apr. 29, 2014, now Pat. No. 9,758,465.

(60) Provisional application No. 61/817,462, filed on Apr. 30, 2013.

(51) Int. Cl.
| | |
|---|---|
| *C07C 69/708* | (2006.01) |
| *A61K 31/5575* | (2006.01) |
| *C07C 67/08* | (2006.01) |
| *A61K 31/558* | (2006.01) |

(52) U.S. Cl.
CPC .......... *C07C 69/708* (2013.01); *A61K 31/558* (2013.01); *A61K 31/5575* (2013.01); *C07C 67/08* (2013.01); *C07C 2603/14* (2017.05)

(58) Field of Classification Search
None
See application file for complete search history.

(56) References Cited

U.S. PATENT DOCUMENTS

| | | | |
|---|---|---|---|
| 2,696,481 | A | 12/1954 | Schneider |
| 4,851,432 | A | 7/1989 | Devlin |
| 6,242,482 | B1 | 6/2001 | Shorr et al. |
| 6,441,245 | B1 | 8/2002 | Moriarty et al. |
| 6,528,688 | B2 | 3/2003 | Moriarty et al. |
| 6,700,025 | B2 | 3/2004 | Moriarty et al. |
| 6,809,223 | B2 | 10/2004 | Moriarty et al. |
| 7,417,070 | B2 | 8/2008 | Phares et al. |
| 9,758,465 | B2 * | 9/2017 | Laing .............. C07C 69/708 |
| 2002/0164274 | A1 | 11/2002 | Jackson et al. |
| 2005/0249697 | A1 | 11/2005 | Uhrich et al. |
| 2009/0281189 | A1 | 11/2009 | Walsh |
| 2010/0137902 | A1 | 6/2010 | Lee et al. |
| 2014/0120058 | A1 | 5/2014 | O'Shea et al. |

FOREIGN PATENT DOCUMENTS

| | | |
|---|---|---|
| EP | 2679227 A1 | 1/2014 |
| WO | WO 2013/024051 A1 | 2/2013 |
| WO | WO 2013/024052 A1 | 2/2013 |
| WO | WO 2013/024053 A1 | 2/2013 |

OTHER PUBLICATIONS

Erdmann et al,. "Synthesis and degradation characteristics of salicylic acid-derived poly(anhydride-esters)," Biomaterials, 2000, 21:1941-1946.
Bhure et al., "Facile and Highly Selective Deprotection of tert-Butyldimehtyl Silyl Ethers using Sulfated SnO₂ as a Solid Catalyst," Synthetic Communications, 2008, 38(3):346-353.
Chakraborti, et. al., "Protic Acid Immobilized on Solid Support as an Extremely Efficient Recyclable Catalyst System for a Direct and Atom Economical Esterification of Carboxylic Acids with Alcohols," J. Org. Chem., 2009, 74, 5967-5974.
Chen et al., "Direct Atom-Efficient Esterification between Carboxylic Acids and alcohols Catalyzed by Amphoteric, Water-Tolerant TiO(acac)₂," J. Org. Chem., 2005, 70:8625-8627.
Crouch, R. D., "Selective deprotection of silyl ethers," Tetrahedron 2013, 69(11):2383-2417.
DiLauro, et al., "Use of Catalycit Fluoride under Neutral Conditions for Cleaving Silicon-Oxygen Bonds," Journal of Organic Chemistry, 2011, 76(18):7352-7358.
Fischer et al., Chemische Berichte 1895, 28: 3252-3258.
Höfle et al., "4-Dialkylaminopyridines as Highly Active Acylation Catalysts," Angewandte Chemie International Edition in English, 1978, 17(8):569-583.
Ishihara et al., "Bulky Diarylammonium Arenesulfonates as Selective Esterification Catalysts," J. Am. Chem. Soc., 2005, 127:4168-4169.
Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem., 2004, 69:1890-1902.
Obata et al., "Single Injection of a Sustained-release Prostacyclin Analog Improves Pulmonary Hypertension in Rats," American Journal of Respiratory and Critical Care Medicine, 2008, 177(2):195-201.
Ohnishi et al., "Inhibition of Lipid Peroxidation by Prostaglandin Oligomeric Derivatives," Prostaglandins Leukotrienes and Essential Fatty Acids, Mar. 1, 1992, 45(3):217-221.

(Continued)

*Primary Examiner* — Jeffrey S Lundgren
*Assistant Examiner* — William Y Lee
(74) *Attorney, Agent, or Firm* — Foley & Lardner LLP

(57) ABSTRACT

Disclosed herein are drug release polymer compounds and compositions comprising prostacyclin compounds of Formula (I), and methods of preparing the same. A preferred polymer has a repeating unit of the following structure:

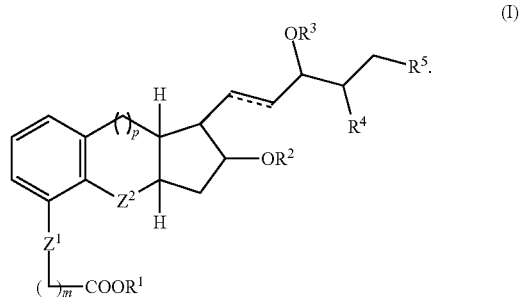

(I)

16 Claims, 7 Drawing Sheets

(56) References Cited

OTHER PUBLICATIONS

Onuma et al., "Ten-year follow-up of the IGAKI-TAMAI stent," EuroIntervention Journal of EuroPCR in collaboration with the Working Group on Interventional Cardiology of the European Society of Cardiology, 2009, 5 Suppl F: F109-111.

Ormiston et al., "Bioabsorbable Coronary Stents," Circulation Cardiovascular Interventions, 2009, 2(3):255-260.

Pasut et al., "PEG conjugates in clinical development or use as anticancer agents: An overview," Advanced Drug Delivery Reviews, 2009, 61(13):1177-1188.

Reepmeyer, John C., "Thermal Decomposition of Aspirin: Formation of Linear Oligomeric Salicylate Esters," Journal of Pharmaceutical Sciences, Mar. 1, 1983, 72(3):322-323.

Shah et al., "A Novel, Chemoselective and Efficient Microwave-Assisted Deprotection of Silyl Ethers with Selectfluor," Journal of Organic Chemistry, 2009, 74(5):2179-2182.

Sharghi et al., "Alumina in Methanesulfonic Acid (AMA) as a New Efficient Reagent for Direct Acylation of Phenol Derivatives and Fries Rearrangement. A Convenient Synthesis of o-Hydroxyarylketones," J. Chem. Research (S), 1998, 628-629.

Tennis et al., "Prostacyclin Inhibits Non-Small Cell Lung Cancer Growth by a Frizzled 9-Dependent Pathway That is Blocked by Secreted Frizzled-Related Protein 1," Neoplasia, 2010, 12(3):244-253.

Wade et al., "Pharmacokinetics of Treprostinil Sodium Administered by 28-Day Chronic Continuous Subcutaneous Infusion," Journal of Clinical Pharmacology, 2004, 44(5):503-509.

Wattamwar et al., "Antioxidant Activity of Degradable Polymer Poly(troloxester) to Suppress Oxidative Stress Injury in the Cells," Adv. Funct. Mater., Nov. 18, 2009, 20(1):147-154.

Woodruff et al., "The return of a forgotten polymer-Polycaprolactone in the 21$^{st}$ Century," Progress in Polymer Science, 2010, 35(10):1217-1256.

\* cited by examiner (I)

Branched homopolymer formed by self-
esterification of unprotected treprostinil

Regular linear homopolymer formed by
self-esterification of ring-hydroxyl-blocked
treprostinil Regular linear homopolymer of treprostinil formed by self-esterification of chain-hydroxyl-blocked treprostinil Heteropolymer formed by esterification of treprostinil in the presence of 6-hydroxyhexanoic acid

CONTROLLED RELEASE PHARMACEUTICAL FORMULATIONS

CROSS-REFERENCE TO RELATED APPLICATIONS

This application is a Divisional of U.S. application Ser. No. 14/264,392, filed Apr. 29, 2014, which claims priority from U.S. Provisional Application No. 61/817,462, filed Apr. 30, 2013, the entire contents of which are incorporated herein by reference.

FIELD

The present invention relates to controlled release formulations of self-polymerizing drug moieties comprising one or more carboxylic acid groups and one or more hydroxyl groups.

BACKGROUND

Polymeric systems for the delivery of bioactive materials such as drugs are well known in the art, but many inherent problems persist and there is a need for a controlled-release pharmaceutical formulation with high loading, precisely controlled drug release and low toxicity.

Variations in blood concentration of a drug can lead to inadequate efficacy if too little drug is present in the blood or at the site of action for any length of time, and to side effects when there is too much drug in the bloodstream or at the site of action. An ideal drug administration modality would achieve a steady concentration of the drug in the 'therapeutic window' sufficient to achieve maximal efficacy while not high enough to engender side effects. In practice, this ideal concentration of drug often transpires to be a compromise between efficacy and side effects. For many drugs (e.g., prostacyclin drugs), the breadth of this therapeutic window is rather narrow. The achievement of a 'flat' concentration profile for treprostinil, for example, is approximated by continuous subcutaneous infusion using a pump and achieves a favorably low peak-to-trough variation of 20-30% (Wade, M., et al., Journal of Clinical Pharmacology, 2004, 44(5): 503-509). However, administration via subcutaneous infusion gives rise to significant injection site pain and inflammation, and administration via indwelling catheter poses a risk of infection. So far, attempts to achieve the objective of having an alternative mode of administration to continuous infusion have not been highly successful. There is, therefore, a need to provide a controlled release formulation which avoids the risk of infection or pain at the infusion site, while achieving a flat concentration profile of drug in the therapeutic window.

U.S. Pat. No. 7,417,070 discloses certain esters, salts, and sustained release oral compositions comprising treprostinil.

U.S. Pat. No. 6,242,482 discloses certain long-acting prostaglandin compositions, some of which include treprostinil.

SUMMARY

In one aspect, a drug release polymer is provided, wherein the polymer includes an active pharmaceutical moiety which comprises at least one carboxylic acid group and at least one hydroxyl group. In some embodiments, the active pharmaceutical moieties form monomeric units covalently bonded to each other to form a polymer backbone, and the active pharmaceutical moieties are capable of being released at a rate that is dependent on the extent of biodegradation of the polymer backbone. In some embodiments, the active pharmaceutical or drug moiety is a prostacyclin compound. In some embodiments, the prostacyclin compound is selected from epoprostenol, treprostinil, beraprost, iloprost, cicaprost, or a prostaglandin I2. In one embodiment, the prostacyclin compound is treprostinil. In a further embodiment, the prostacyclin compound has the following structure (I)

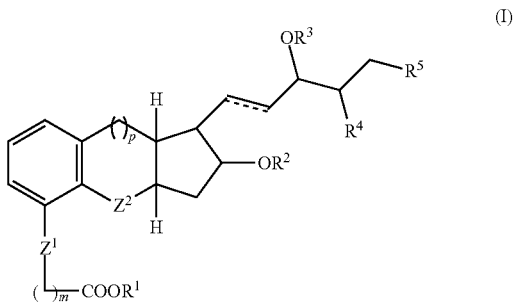

(I)

wherein

⁀ represents a single or a double bond;

$Z^1$ and $Z^2$ each independently represents an O or $CH_2$;

p=0 or 1;

m=1, 2, or 3;

$R^1$ represents a H or an acid protective group;

$R^2$ and $R^3$ each independently represents a H or a hydroxyl protective group;

$R^4$ represents H and the other represents a $C_{1-6}$ alkyl; and $R^5$ represents a $C_{1-6}$ alkyl group or $C_{2-8}$ alkynylene group.

The prostacyclin compound forms various configurations of drug release polymers via formation of ester bonds between the carboxylic acid group on one prostacyclin molecule and the hydroxyl group on the other prostacyclin molecule. In some embodiments, in addition to the prostacyclin compound, the polymer also includes a co-monomer covalently bonded to the carboxylic acid group of one drug moiety and the hydroxyl group of a second drug moiety. In some embodiments, the co-monomer is 6-hydroxyhexanoic acid or hydroxyl-polyethylene glycol-carboxylic acid.

In one embodiment, the recurring unit in the polymer has a structure selected from the group consisting of Formula (IIa), (IIb) and (IIc):

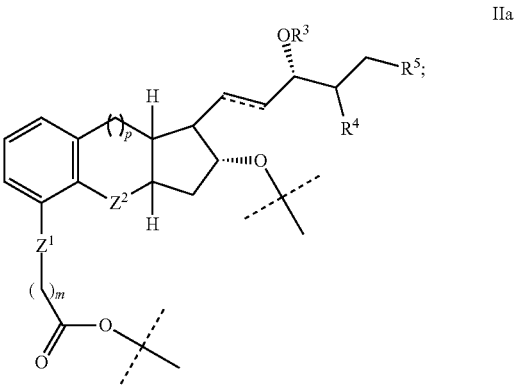

IIa

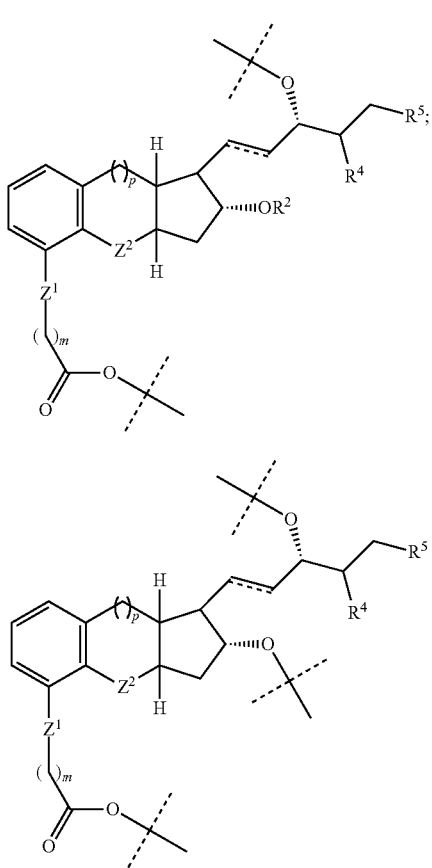

In another aspect, a pharmaceutical composition comprising the drug release polymer and a pharmaceutically acceptable excipient is provided. In some embodiments, upon administration of the pharmaceutical composition to a patient, the drug release polymer degrades initially into inert polymer fragments, which thereafter give rise to active drug only after a time interval. In some embodiments, the pharmaceutical composition exhibits accelerating release of the drug moiety. In some embodiments, the pharmaceutical composition is used as a medicament for injection, preferably subcutaneous or intramuscular injection. In other embodiments, the pharmaceutical composition is used as a medicament for implant.

In still another aspect, a method is provided for producing a drug release polymer, comprising esterifying a drug moiety which comprises at least one carboxylic acid group and at least one hydroxyl group prostacyclin compound in the presence of a coupling agent and a catalyst. In some embodiments, the coupling agent is N-(3-Dimethylaminopropyl)-N'-ethylcarbodiimide or N,N'-Dicyclohexylcarbodiimide. In other embodiments, the catalyst is 4-(Dimethylamino)pyridine. In some embodiments, the method further comprises blocking one or more carboxylic acid groups in excess of one carboxylic group, prior to esterification. In other embodiments, the method further comprises blocking one or more hydroxyl groups, in excess of one hydroxyl group, prior to esterification. In some embodiments, the one or more hydroxyl groups are blocked using trimethylsilyl chloride or t-butyldimethylsilyl chloride.

In another aspect, a method is provided for treating, controlling, delaying or preventing in a mammalian patient in need of the treatment of one or more conditions comprising administering to said patient a diagnostically and/or therapeutically effective amount of the drug release polymer or a pharmaceutical composition containing the drug release polymer. In a preferred embodiment, the drug moiety is treprostinil, and the method is a method for treating pulmonary hypertension in a patient in need thereof.

DETAILED DESCRIPTION

Figure 1:
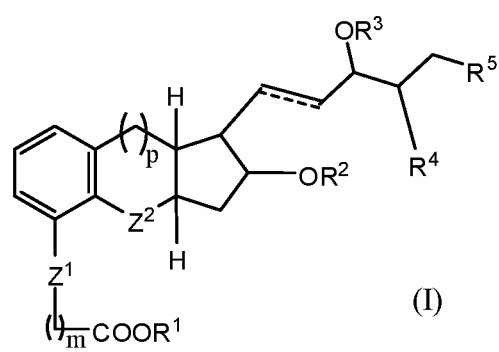
FIG. 1 shows one embodiment of the structure of a drug moiety forming a repeating unit in the polymer.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The expression "comprising" means "including, but not limited to." Thus, other non-mentioned substances, additives, carriers, or steps may be present. Unless otherwise specified, "a" or "an" means one or more.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, $C_{m\text{-}n}$, such as $C_{1\text{-}12}$, $C_{1\text{-}8}$, or $C_{1\text{-}6}$ when used before a group refers to that group containing m to n carbon atoms.

The term "alkoxy" refers to O-alkyl.

As used herein, "halo" or "halogen" or even "halide" can refer to fluoro, chloro, bromo, and iodo.

The term "alkyl" refers to monovalent saturated aliphatic hydrocarbyl groups having from 1 to 12 carbon atoms (i.e., $C_1$-$C_{12}$ alkyl) or 1 to 8 carbon atoms (i.e., $C_1$-$C_8$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom.

Combinations of substituents and variables are only those that result in the formation of stable compounds. The term "stable," as used herein, refers to compounds which possess stability sufficient to allow manufacture and which maintains the integrity of the compound for a sufficient period of time to be useful for the purposes detailed herein.

As used herein, the term "prodrug" means a derivative of a compound that can hydrolyze, oxidize, or otherwise react under biological conditions (in vitro or in vivo) to provide an active compound. Examples of prodrugs include, but are not limited to, derivatives of a compound that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate).

As used herein, "hydrate" is a form of a compound wherein water molecules are combined in a certain ratio as an integral part of the structure complex of the compound.

As used herein, "solvate" is a form of a compound where solvent molecules are combined in a certain ratio as an integral part of the structure complex of the compound.

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included are pharmaceutically acceptable salts or compounds of any of the Formulae herein.

Depending on its structure, the phrase "pharmaceutically acceptable salt," as used herein, refers to a pharmaceutically acceptable organic or inorganic acid or base salt of a compound. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

As used herein, "protecting group" or "protective group" is used as known in the art and as demonstrated in Greene, *Protective Groups in Organic Synthesis*.

As used herein, "hydroxyl protective group" or "hydroxyl protecting group" or "hydroxyl blocking group" refers to the generally understood definition of an alcohol or hydroxyl protecting group as defined in T. W. Greene, *Protective Groups in Organic Synthesis*, John Wiley and Sons, 1991 (hereinafter "Greene, *Protective Groups in Organic Synthesis*").

As used herein, "acid protective group" or "acid protecting group" or "carboxylic acid blocking group" refers to the generally understood definition of protection for the carboxylic acid group as defined in T. W. Greene, *Protective Groups in Organic Synthesis*, John Wiley and Sons, 1991 (hereinafter "Greene, *Protective Groups in Organic Synthesis*").

In various aspects, drug polymers are provided for sustained release of an injected or implanted drug in order to achieve favorable pharmacokinetics with minimal peak-to-trough variation of drug concentration in the blood. The drug polymers are designed to achieve a better approximation of the ideal continuous, steady, blood concentration profile which is approached most closely by continuous drug infusion, and which is difficult to achieve with current sustained release methodologies.

The present technology is adaptable to any drug containing one or more carboxylate groups and additionally one or more hydroxyl groups (i.e., primary or secondary alcohols). In the drug release polymer, the drug itself acts as a monomer. Therefore, in one embodiment, the only ingredient in the polymer is the drug molecule, minus abstracted water molecules generated in the formation of ester bonds during polymer formation. The ester bonds, being metastable, will hydrolyse in the presence of water in body fluids following administration, causing breakdown of the polymer, resulting in the re-generation of monomeric drug molecule from the inactive polymer prodrug, in a staged manner, via oligomeric, inactive, intermediates.

Prostacyclin compounds are an example of a drug containing one or more carboxylate groups and one or more hydroxyl moieties. These include both stable prostacyclin compounds such as treprostinil and beraprost (and the 314d active isomer of beraprost) and less-stable prostacyclin compounds such as prostacyclin (prostaglandin-$I_2$) itself.

In the case of prostacyclin compounds, existing drug-polymer reversible-covalent conjugates (such as PEG-drug conjugates of the type described by Pasut, G. and F. M. Veronese, *Advanced drug delivery reviews*, 61(13): 1177-1188, 2009) for bolus injection, and those that are described in patents and applications by Ascendis Pharma (WO 2013/024051, WO 2013/024052, WO 2013/024053), prolong the absorption phase and also the elimination phase of the drug from the bloodstream, resulting in improved longevity in the blood of a drug molecule. However, in these systems (designed to create a circulating reservoir of the drug in the bloodstream), the drug concentration in the blood inevitably undergoes an exponential decline shortly after the attainment of a maximal blood concentration (Cmax). This exponential decay prevents the drug ever achieving a true 'zero-order' release kinetic, wherein there is a constant blood concentration. During the decay phase, hydrolysis of the drug-polymer bond takes place at a fixed rate, leading the polymer-delivered drug to follow a somewhat faster elimination kinetic than the polymer conjugate (although much slower than that of the free drug), based on its shorter half-life as a free compound. Rather than follow a 'saw-tooth' blood concentration profile, which is the case for free compound in non-sustained release formulations, whether inhaled, ingested or injected (bolus), the classical covalent-release drug conjugate has a smoother, more undulating concentration profile in the blood. Nevertheless, the significant peak-to-trough variation in blood concentration that remains may not be markedly better than other alternative modes of sustained delivery of the free compound (such as sustained release oral tablet formulations), resulting in periods of inadequate efficacy or undesirable toxicity of the drug, when blood concentrations are in 'trough' or 'peak' zones (respectively). The new drug polymers of the present technology provide solutions to the problem of residual peak-to-trough variation inherent in existing drug-polymer conjugate systems.

In one aspect, a drug release polymer is provided, wherein the polymer includes a drug moiety which comprises at least one carboxylic acid group and at least one hydroxyl group. In some embodiments, the drug moiety is a prostacyclin compound. In some embodiments, the drug release polymer is a controlled release polymer. In some embodiments, the drug moieties form monomeric units that are covalently bonded to each other to form the polymer backbone, and wherein the drug moieties are capable of being released in a manner dependent upon the extent of breakdown of the polymer backbone. Thus, the drug moiety is an integral part of the polymeric chain and is embedded and comprises the fabric of the polymer. This feature distinguishes the polymers of the present invention from prior drug polymer covalent sustained release systems, wherein the polymer is made from a different substance (e.g. PEG made from ethylene glycol) than that of the drug.

In some embodiments, the drug release polymer includes linear and branched homopolymers and heteropolymers of a prostacyclin compound. Any prostacyclin which has one or more carboxylic acid group and one or more hydroxyl group can be utilized for the drug release polymer. Examples of such prostacyclin compounds include, but are not limited to, epoprostenol, treprostinil, beraprost, iloprost, cicaprost, prostaglandin I2. In one embodiment, the prostacyclin compound is treprostinil. In another embodiment, the prostacyclin compound is beraprost.

In one embodiment, the prostacyclin compound has the following structure (I)

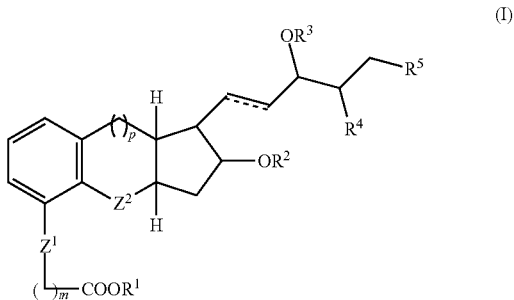

wherein

⁂ represents a single or a double bond;
$Z^1$ and $Z^2$ each independently represents an O or $CH_2$;
p=0 or 1;
m=1, 2, or 3;
$R^1$ represents a H or an acid protective group;
$R^2$ and $R^3$ each independently represents a H or a hydroxyl protective group;
$R^4$ represents H and the other represents a $C_{1-6}$ alkyl; and
$R^5$ represents a $C_{1-6}$ alkyl group or $C_{2-8}$ alkynylene group.

In some embodiments, $Z^1$ is a O and $Z^2$ is $CH_2$. In some embodiments, $Z^1$ is $CH_2$ and $Z^2$ is O.

In some embodiments, $R^1$ is H. In other embodiments, $R^1$ is an acid protective group. Suitable carboxylic acid protective groups $R^1$ are known in the art and include the ester derivatives of a carboxylic acid group commonly employed to block or protect the carboxylic acid group while reactions are carried out on other functional groups on the compound. Exemplary groups for the protection of the carboxylate group include allyl, methyl, ethyl, nitrobenzyl, dinitrobenzyl, tetrahydropyranyl, methoxybenzyl, dimethoxybenzyl, trimethoxybenzyl, trimethylbenzyl, pentamethylbenzyl, methylenedioxybenzyl, benzhydryl, 4,4' dimethoxybenzhydryl, 2,2'4,4'-tetramethoxybenzhydryl, t-butyl, t-amyl, trityl, 4 methoxytrityl, 4,4'-dimethoxytrityl, 4,4',4"-trimethoxytrityl, 2-phenyl-prop-2-yl, trimethylsilyl, t-butyldimethylsilyl, phenacyl, 2,2,2-trichloroethyl, b-(tri-methylsilyl)ethyl, b (di (n-butyl)methylsilyl)ethyl, p-toluenesulfonylethyl, 4-nitrobenzylsulfonylethyl, cinnamyl, 1-(trimethylsilylmethyl) prop-1-en-3-yl, and like moieties. In some embodiments, $R^1$ is a benzyl, tertiary-butyl, dimethoxy benzyl, nitrobenzyl or a dinitrobenzyl group.

In some embodiments, $R^2$ and $R^3$ each independently is a H. In other embodiments, $R^2$ and $R^3$ each independently is a hydroxyl protective group. Suitable groups for the protection of the hydroxyl groups are known in the art and include, but are not limited to, methyl, t-butyl, tetrahydropyranyl, benzyl, methoxybenzyl, nitrobenzyl, tertiary butyl dimethyl silyl (TBDMS), trimethylsilyl (TMS), tertiary methyl dimethyl silyl group, methoxymethyl, methoxyethoxymethyl, allyl, trityl, ethoxyethyl, 1-methyl-1-methoxyethyl, tetrahydropyranyl, or tetrahydrothiopyranyl group. In one embodiment, the hydroxy protective group is tetrahydropyranyl (THP). In some embodiments, $R^2$ and $R^3$ each independently is a tetrahydropyranyl, benzyl, methoxybenzyl, nitrobenzyl, tertiary butyl dimethyl silyl or a tertiary methyl dimethyl silyl group.

In some embodiments, m is 1 and p is 1. In other embodiments, m is 3 and p is 0.

The prostacyclin compound forms various configurations of drug release polymers via formation of ester bonds between the carboxylic acid group on one prostacyclin compound and the hydroxyl group on the other prostacyclin compound. For example, with treprostinil, the drug can be designed to be a homopolymer in three basic forms, or a number of heteropolymer variants made with different co-monomers. Treprostinil is the active ingredient in Remodulin®, and is described in Moriarty, et al in *J. Org. Chem.* 2004, 69, 1890-1902, U.S. Pat. Nos. 6,441,245, 6,528,688, 6,700,025, and 6,809,223, which are incorporated by reference in their entirety. Treprostinil has the following structure (II):

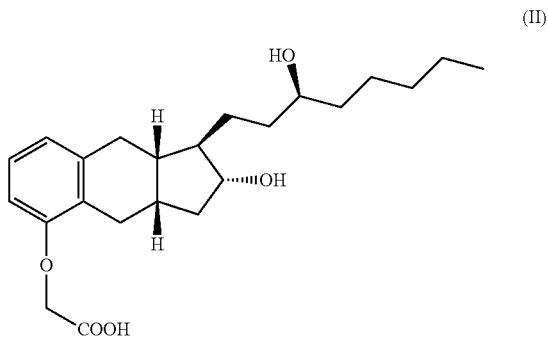 [SMILES: CCCCC[C@H](O)CC[C@@H]1[C@H]2Cc3cccc(OCC(=O)O)c3C[C@H]2C[C@H]1O]

Treprostinil has one carboxylic acid group and two hydroxyl groups—one ring hydroxyl group and one chain hydroxyl group. Various homopolymers and heteropolymers can result from the reaction between the carboxylic group with either the ring hydroxyl or the chain hydroxyl group of various treprostinil moiety to form esters. Blocking agents can be used to selectively block either the ring hydroxyl or the chain hydroxyl group resulting in the formation of various linear or branched homopolymers. FIG. 1 shows a structure of a preferred drug moiety forming a repeating unit in the polymer, wherein the letter variables of the formula have the same meaning set forth in paragraph 6. Exemplary homopolymers and heteropolymers of treprostinil are depicted in FIGS. 2-6, wherein all inter-monomer bonds are ester bonds.

The drug release polymers of the present technology function as prodrugs, whereby they release the pharmacologically active form of the drug moiety by cleavage of the temporary ester group linkages formed between the drug moieties.

The drug release polymers of the present technology have a polarity, just like important biopolymers such as DNA, RNA and protein. Whereas nucleic acids have a 5' and a 3' end, and proteins have an N-terminus and a C-terminus, which dictate their direction of growth during biosynthesis, so the present polymers have a 'carboxylate end' and a 'hydroxyl end.' Polymer chain length can be controlled by various methods known in the art, e.g., by incorporating various amounts of chain terminating reagents. In some embodiments, a drug moiety with carboxylate protection (methyl, nitrile) can be used to form the end of a polymer. Increasing amounts of such chain terminating agents incorporated into a polymerization mixture would give rise to shorter polymer lengths on average. In other embodiments, a drug moiety with two blocked hydroxyls and a free carboxylate can be used to limit the length of the polymer. In yet other embodiments, incorporation of methanol or ethanol (or other primary, secondary or tertiary alcohols) into the reaction mixture after an interval can be used to stop the polymerization reaction. The time at which the reaction is stopped can be altered to create polymers of different lengths. In general, longer reaction times will result in longer polymers. It may or may not be appropriate or necessary to remove the chain terminating groups. For example, a methyl ester blocking group on a carboxylate could be left on, whereas a tertiarybutyldimethylsilane, which can be toxic if liberated, can be removed before administration to humans. Various types of chain terminating compounds can be used, including those that stop chain elongation at the 'carboxylate end,' and those that stop chain elongation at the 'hydroxyl end,' or a mixture of the two can be used if needed. Chain length can also be controlled by controlling the esterification reaction time.

The drug release polymer can have any suitable length depending on the desired physiochemical property or the mode of administration. Polymer properties are described below with parameters defined by the International Union of Pure and Applied Chemistry (IUPAC) wherein the range of molecular weights in a non-uniform mixture of chemically similar polymer molecules (i.e. 'dispersity') is represented by the symbol 'Đ' which can refer to either molecular mass or degree of polymerization. It can be calculated using the equation $Đ_M=M_w/M_n$, where $M_w$ is the weight-average molar mass and $M_n$ is the number-average molar mass. Exemplary polymer lengths can include chain lengths from about n=2 (i.e. dimer, where all molecules have two monomeric moieties and there is no dispersity) up to Mn=5000 wherein there is a distribution of polymer lengths or 'dispersity'. For forms of the polymer having finite dispersity, $Đ_M$ may conveniently be in the range 1.1-1.3. Where it is particularly important to have a rather uniform distribution of polymer lengths, e.g. for an accelerating release soluble polymer designed to form a circulating depot in the bloodstream, this may be controlled during polymerization by the timed addition of suitable terminating agents, such as those described herein, to achieve values of $Đ_M$ in the range 1.01-1.1

In still another aspect, a method for producing a drug release polymer is provided. In some embodiments, the method comprises esterifying a monomeric drug moiety which has one or more carboxylic acid groups and one or more hydroxyl groups. In some embodiments, the method comprises esterifying a prostacyclin compound.

Suitable drug candidates for polymer formation by ester bond formation, include drugs which have at least one alcohol (hydroxyl) group, and at least one carboxylate group. In some embodiments, the drug has two or more hydroxyl groups. In some embodiments, if the drug has more than one hydroxyl group, most favorably it does not have more than one carboxylate because this may result in the formation of non-extendible dimers rather than the desired polymeric product. In some embodiments, the drug has more than one carboxylate groups and one hydroxyl group. In such cases, protection of the additional carboxylate groups is required in order to allow for productive polymer formation.

The various polymer types described herein can have differing degrees of polymerization, from dimer to trimer and beyond, to potentially contain hundreds of monomeric moieties per polymer. All of these polymers, including small oligomers, such as dimer and trimer, can be useful for drug delivery purposes. In their simplest form, where the only monomeric ingredient is drug molecule, these polymers or prodrugs have the unique quality of having no additional chemical moieties over and above the original drug substance. Therefore, their toxicological properties would not vary significantly from the original drug substance. In the case of prostacyclin compounds, such as those described herein, their dose-limiting toxicity would be the pharmacological toxicity of the prostacyclin class of compounds. Such adverse effects, if any, can be managed more effectively by sustained or accelerating release of the drug from the polymer.

Suitable esterification process conditions are known in the art. In one embodiment, the esterification process is conducted using the Steglich esterification reaction. In some embodiments, the method comprises esterifying a prostacyclin compound in the presence of a coupling agent and a catalyst. In some embodiments, the coupling agent is N-(3-Dimethylaminopropyl)-N'-ethylcarbodiimide or N,N'-Dicyclohexylcarbodiimide. In some embodiments, the catalyst is 4-(Dimethylamino)pyridine. In some embodiments, the polymerization reaction is conducted using a Steglich esterification process as described by Höfle, G., W. Steglich, et al. Angewandte Chemie International Edition in English, 1978, 17(8), 569-583. Such reactions have been reported to attach protected drugs to linker moieties (WO 2013/3024051, WO 2013/3024052, WO 2013/3024053) in order to achieve a defined metastable ester linkage between a linker and the drug moiety and to allow subsequent conjugation of this assembly to a polymer. Conversely, the aim of the present technology is to create a drug polymer, wherein the monomers are primarily drug molecules, and comprise part of the backbone of the polymer and do not comprise (or predominantly do not comprise) appendages on the end of a polymer chain. Fewer reactions are required to achieve the drug-polymers of the present invention. An alternative method of polymer formation is to conduct the polymerizing esterification reaction using acidic alumina and methanesulfonic acid ($Al_2O_3/MeSO_3H$ (AMA)) as described in detail by Sharghi et al. (H. Sharghi, Babak Kaboudin, J. Chem. Research (S), 1998, pp. 628-629). This method is particularly suited to creating monoesters from a carboxylate compound and a diol, such as ethylene glycol. however it should be recognized in the present invention that prostacyclin drugs such as treprostinil and beraprost, having both carboxylate and diol functionalities in the same molecule, in the absence of other extraneous diol compound, and unlike the compounds studied by Sharghi, will polymerize. Unlike Steglich esterification, which can be conducted at room temperature, the Sharghi method requires heating at about 80° C. According to this method $Al_2SO_3$ (a solid) and $MeSO_3H$ (a liquid) are used in molar ratio of 1:5 at 80° C. for between 7 and 120 mins, or until an acceptable yield of product is obtained.

In some embodiments, wherein the drug moiety includes more than one carboxylic acid or hydroxyl group, the method further comprises blocking one or more of the additional carboxylic acid and/or hydroxyl groups. In some embodiments, the method further comprises blocking one or more of the additional carboxylic acid groups. In other embodiments, the method further comprises blocking one or more of the additional hydroxyl groups.

For a drug having one carboxylate group and at least one alcohol group (such as a primary or secondary alcohol), the polymer can be prepared by ester bond formation methods known in the art. For example, the drug can be acidified in aqueous solution using a strong acid such as, e.g., para-toluenesulfonic acid or sulfuric acid, upon which it will undergo Fischer esterification (Emil Fischer, Arthur Speier, *Chemische Berichte* 1895, 28: 3252-3258). para-Toluenesulfonic acid (a solid) is preferred over sulfuric acid (a liquid), since it lacks the oxidizing properties of the latter and may conveniently be weighed. In some embodiments, the acidification is conducted in aqueous medium at a pH less than 2.0, e.g., pH approx 1.0 in aqueous para-Toluenesulfonic acid at a concentration of 0.5 M. In general, for ester bond formation with non-polymerizing reactants (e.g., ethanol and acetic acid to form ethyl acetate), in the presence of strong acid, an equilibrium is reached and the reaction does not go to completion. However, in the present invention, since the resulting drug homopolymer (or heteropolymer formed from 6-hydroxy-hexanoic acid and drug) is likely to be insoluble, it will be removed from the aqueous reaction mixture by spontaneous precipitation while forming, which will inhibit the reverse reaction, tending to drive the reaction towards completion. The precipitated polymer may be recovered by filtration and washing with water to remove para-Toluenesulfonic acid. Heating, up to about 80° C., may be required to drive the reaction, which may require from 1 to 8 hours to give acceptable yield.

A variety of catalysts can be used to facilitate ester bond formation, which will be useful for the formation of the drug polymers of the present invention. Recent literature in this field is summarized at http://www.organic-chemistry.org/namedreactions/fischer-esterification.shtm and applicable methods are summarized herein. In the following schemes, OH—R' represents either the ring or chain hydroxyl of a prostacyclin drug molecule, with R' representing the remainder of the molecule. The other reactant represents the carboxylate end of a second prostacyclin molecule. 'R' represents the moiety of a prostacyclin molecule except for the carboxylate.

K. Ishihara, S. Nakagawa, A. Sakakura, J. Am. Chem. Soc., 2005, 127, 4168-4169.

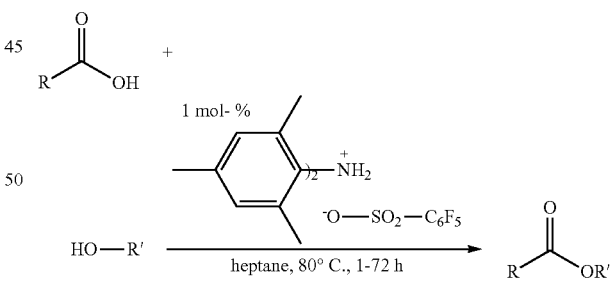

T. Chen, Y. S. Munot, J. Org. Chem., 2005, 70, 8625-8627.

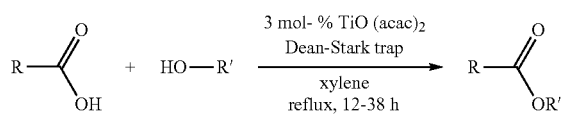

A. K. Chakraborti, et. al., J. Org. Chem., 2009, 74, 5967-5974.

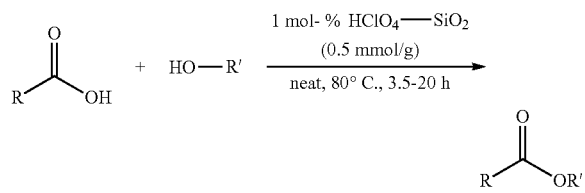

In some embodiments, the polymer forming esterification reactions can be conducted at or near room temperature in order to avoid damage to the monomer and polymeric material. In some embodiments, the esterification reactions are conducted at suitable temperature, e.g., at about 100° C. or below, at about 80° C. or below, at about 70° C. or below, at about 60° C. or below, at about 50° C. or below, at about 40° C. or below, at about 30° C. or below, or at about 25° C. or below. In some embodiments, the esterification reaction is conducted at room temperature. In some embodiments, the esterification reaction is conducted at about 25° C.

Figure 2:
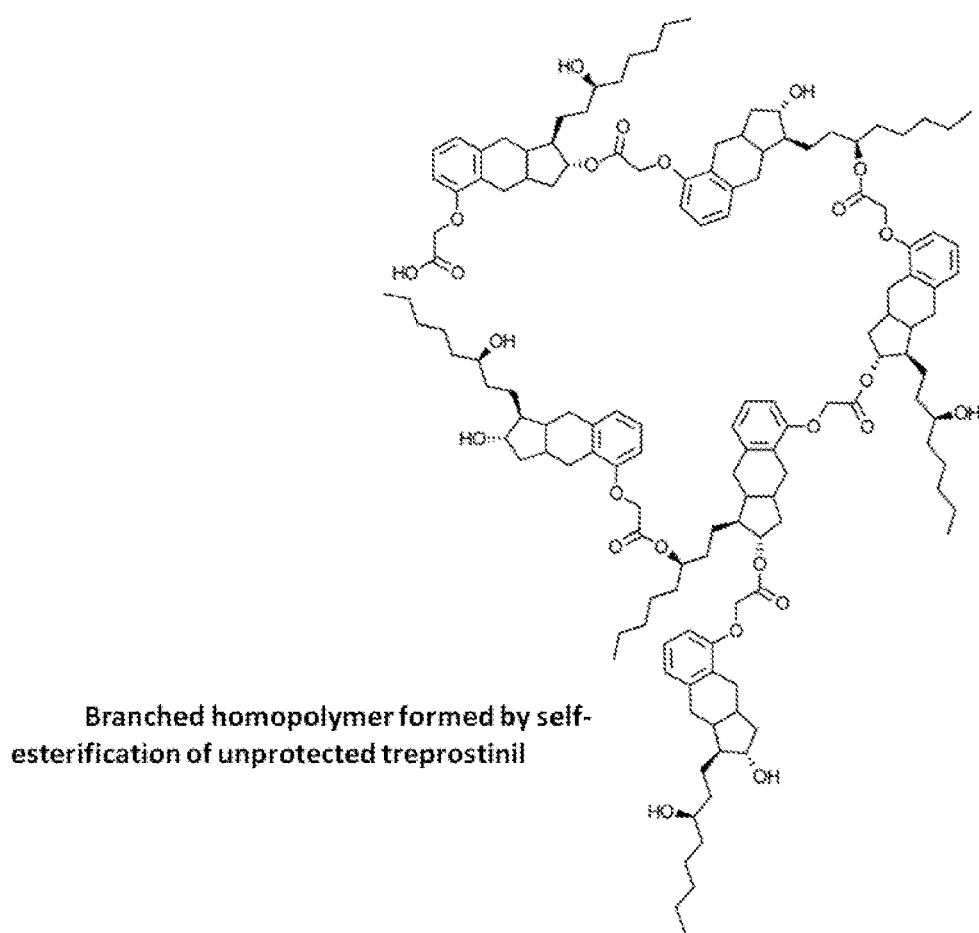
FIG. 2 shows one embodiment of the polymer of the invention, wherein both the ring hydroxyl and the chain hydroxyl of treprostinil are involved in backbone bonds of the polymer leading to a branched structure.

Conducting the esterification in the presence or absence of a blocking agent will result in a variety of drug release polymers. For example, in one embodiment, polymerization of treprostinil, e.g., via a Steglich esterification reaction, in the absence of blocking agents on the treprostinil molecule, gives rise to a branched polymer (FIG. 2). In this form of the polymer, both the ring hydroxyl and the chain hydroxyl become involved in backbone bonds of the polymer leading to a branched structure.

Figure 3:
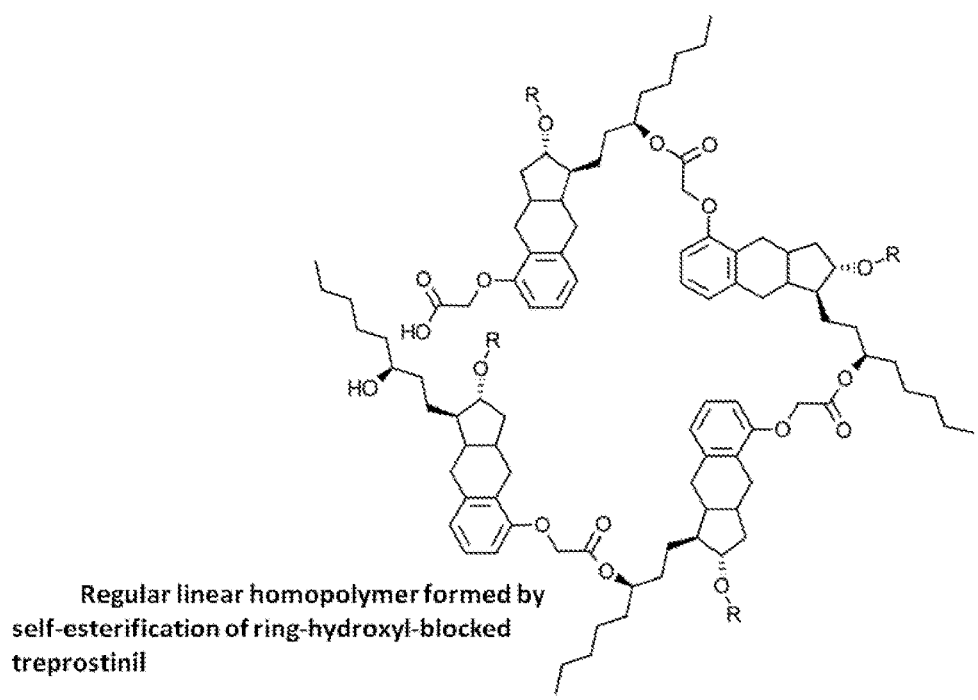
FIG. 3 shows one embodiment of a linear polymer formed by utilizing a 'ring-hydroxyl-blocked' form of treprostinil and involving only the chain hydroxyl and not the ring hydroxyl.

In one embodiment, a linear polymer can be formed is using a 'ring-hydroxyl-blocked' form of prostacyclin. This is because the ring hydroxyl is the more reactive of the two hydroxyls, and its selective blockade is easier to achieve. First the carboxylate must be temporarily protected, in order to prevent reaction of the carboxylate with the hydroxyl-blocking reagent. FIG. 3 depicts a linear polymer formed by utilizing a 'ring-hydroxyl-blocked' form of treprostinil and involving only the chain hydroxyl and not the ring hydroxyl. The lesser reactivity of the available chain-hydroxyl groups (compared to the ring hydroxyl groups) will lead to slower reaction rates for this type of polymer.

Figure 4:
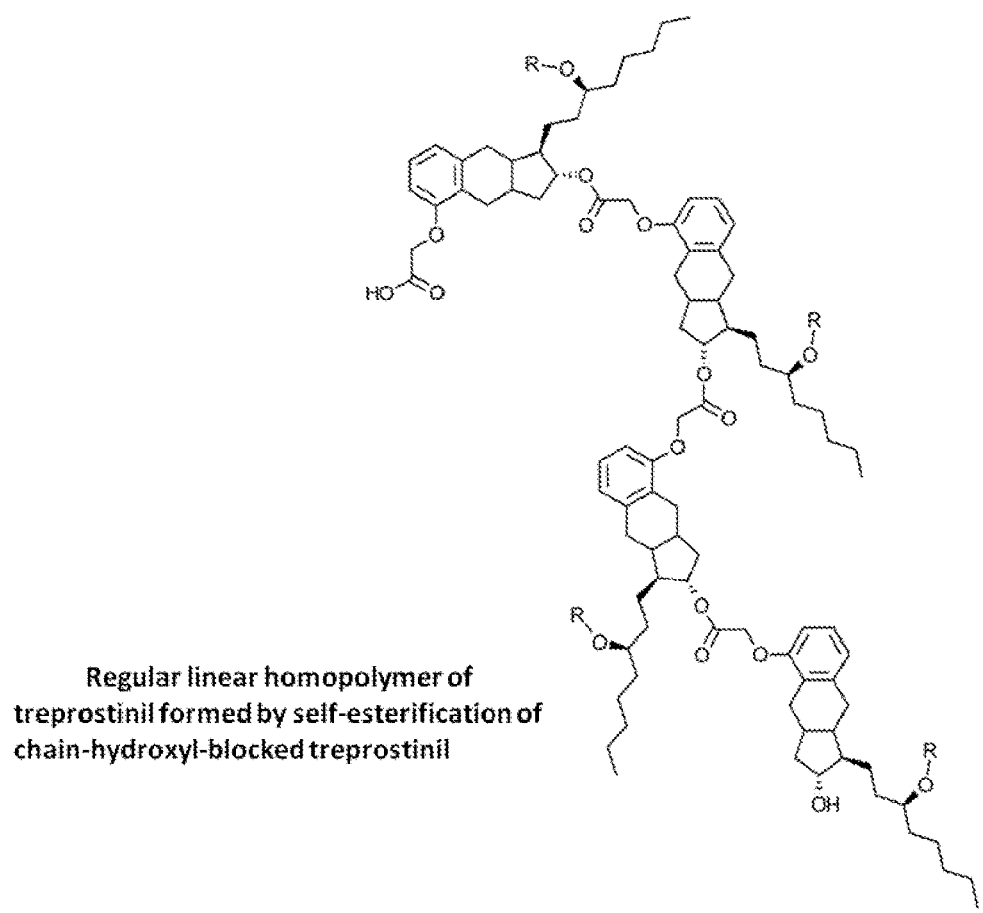
FIG. 4 shows another embodiment of a linear polymer formed by utilizing a 'chain-hydroxyl-blocked' form of treprostinil and involving only the ring hydroxyl and not the chain hydroxyl.

In another embodiment, the chain-hydroxyl group can be blocked following the temporary protection of the carboxylate group, leading to the formation of another linear polymer depicted in FIG. 4. The rate and extent of polymerization of this form is anticipated to be greater than for the other homopolymers.

In embodiments where the polymers are made from blocked forms of treprostinil, the blocking or protective group can either be removed or retained on the polymer. In some embodiments, removal of the blocking or protective group after polymerization, under conditions that do not hydrolyze or otherwise break the ester bonds, will give rise to different forms of regular (i.e., linear or unbranched) drug homopolymer. In cases where the protective group is not toxic, it can be left on, and the protected drug polymer used as a therapeutic agent. The protective group will likely undergo a slow spontaneous aqueous hydrolysis in vivo. In cases where the protective group is toxic, it must first be removed before the polymer can be used as a therapeutic agent.

Various blocking agents and blocking strategies to achieve the necessary selective blockade of ring or chain hydroxyl groups are known in the art. Further, blocking or protective groups which are amenable to deprotection under mild conditions, conducive to maintenance of stability of the polymer and its drug moieties are desirable. In some embodiments, linear polymers may be formed by the use of protecting groups to temporarily block the reactivity of particular target groups in the prostacyclin or prostacyclin-drug molecule. In some embodiments, the linear polymers are prepared by creating prostacyclin structures wherein only one of the two hydroxyl (alcohol) groups is blocked (i.e., the ring hydroxyl and the chain hydroxyl), leaving a molecule in which there are exposed a single reactive carboxylate and a single reactive hydroxyl.

In some embodiments it may also be necessary to temporarily block the carboxylate group in order to allow an appropriate series of protection and deprotection reactions to prepare a single-hydroxyl-blocked form. Suitable groups for the protection or blocking of hydroxyl and carboxylate group are known in the art and are disclosed herein. Furthermore, particular ester groups that allow selective removal of carboxylate-protecting groups by enzymatic methods are known in the art, and include, but are not limited to heptyl esters ($C_7H_{15}O_2CR$), 2-N-(morpholino) ethyl esters, choline esters ($Me_3N^+CH_2CH_2O_2Br$) (Sander, J. and H. Waldmann 2000, Chemistry-A European Journal 6(9), 1564-1577), (methoxyethoxy) ethyl esters and methoxyethyl esters (CH3OCH2CH2O2CR). These groups can be cleaved under very mild conditions, for example, enzymatic hydrolysis (Wuts, P. G. M., and Greene, T. W., 2007, Greene's Protective Groups in Organic Synthesis. New Jersey, John Wiley & Sons, Inc; hereinafter Wuts 2007). These enzymatically-cleavable carboxylate blocking strategies may be particularly effective in creating mono-hydroxy-protected forms of prostacyclin drugs for the formation of linear polymers.

Several suitable blocking or protective groups for the hydroxyl groups of the prostacyclin drugs which may be removed under mild conditions conducive to maintenance of polymer stability are known in the art (e.g., Wuts 2007; Crouch, R. D., Tetrahedron 2013, 69(11): 2383-2417, hereinafter Crouch 2013). In some embodiments, the hydroxyl blocking or protective group is a silyl ether group. Suitable silyl ether blocking groups include, e.g., trimethylsilyl (TMS), t-butyldimethylsilyl (TBDMS), introduced as the chlorides TMSCl, TBDMSCl, which are spontaneously and selectively reactive towards hydroxyl groups. The chloride forms react under mild conditions conducive to stability of the drug molecule (e.g., TBDMSCl, imidazole, dimethylformamide, 25° C., 10 h). As will be apparent to one skilled in the art, the differential reactivity of different hydroxyl groups in a compound can be utilized to achieve selective blockade of one hydroxyl as opposed to other hydroxyl groups in the compound (Wuts 2007). In some embodiments, the blocking groups can be utilized to selectively block the more-reactive ring hydroxyl compared. In other embodiments, the blocking groups can be utilized to selectively block the chain hydroxyl of a prostacyclin compound.

Suitable groups for the blocking or protecting the carboxylic acid groups are known in the art and include, but are not limited to, allyl, methyl, ethyl, nitrobenzyl, dinitrobenzyl, tetrahydropyranyl, methoxybenzyl, dimethoxybenzyl, trimethoxybenzyl, trimethylbenzyl, pentamethylbenzyl, methylenedioxybenzyl, benzhydryl, 4,4' dimethoxybenzhydryl, 2,2'4,4'-tetramethoxybenzhydryl, t-butyl, t-amyl, trityl, 4 methoxytrityl, 4,4'-dimethoxytrityl, 4,4',4''-trimethoxytrityl, 2-phenyl-prop-2-yl, trimethylsilyl, t-butyldimethylsilyl, phenacyl, 2,2,2-trichloroethyl, b-(tri-methylsilyl)ethyl, b (di (n-butyl)methylsilyl)ethyl, p-toluenesulfonylethyl, 4-nitrobenzylsulfonylethyl, cinnamyl, 1-(trimethylsilylmethyl)

prop-1-en-3-yl, and like moieties. In one embodiment the carboxylic acid blocking or protective group is the 2-N-(morpholino)ethyl ester, which is removable enzymatically.

Selective blockade can be achieved as follows, using treprostinil as an example. By reacting carboxylate-protected treprostinil with TBDMS or TMS under gentle conditions (e.g., TBDMSCl, DMAP, Et$_3$N, DMF, 25° C., 12 h), using stoichiometric amounts or modest molar excess of blocking agent, it will be possible to obtain selective derivatization of the ring hydroxyl. Enzymatic removal of the carboxylate protection would then yield a treprostinil derivative with free chain hydroxyl but with a blocked ring-hydroxyl and having a free carboxylate. Such a process would be conducive to producing a linear polyester polymer (or co-polymer), wherein only the chain hydroxyl is involved in formation of the backbone ester bonds. Subsequent deprotection would yield a linear polymer devoid of protecting groups.

In one embodiment, selective blockade of the chain hydroxyl group can also be achieved by taking advantage of the differential base lability of TBDMS and TMS ethers. For example, TBDMS ether groups are known to be 10$^4$ times more stable to basic hydrolysis than the TMS ether groups. Reaction of carboxylate-blocked treprostinil under the gentle conditions with TMSCl, as discussed herein, will yield a treprostinil molecule with a TMS ether on the ring hydroxyl. Further reaction with TBDMS will produce a double-blocked molecule wherein the chain hydroxyl is blocked with TBDMS. Subsequent enzymatic deprotection of the carboxylate followed by deprotection of the double-hydroxyl-protected treprostinil under mild base conditions will yield a treprostinil molecule wherein the chain hydroxyl is blocked, but the ring hydroxyl is free. Polymerization of the latter form of mono-hydroxyl-protected treprostinil under suitable esterification conditions, e.g., by Steglich esterification, will give rise to a polymer wherein only the ring hydroxyl groups participate in ester bond formation, and form part of the backbone of the polymer. Subsequent removal of the remaining TBDMS group will give rise to a polymer wherein the only constituents are treprostinil moieties. Various strategies for the selective protection and deprotection of multiple hydroxyls using silyl ethers are known in the art (e.g., Crouch, 2013), some which are suitable for the removal of protective groups such as TBDMS groups from the polymer.

Suitable mild conditions for deprotection of the linear homopolymers include those which avoid breakage of the inter-monomer ester bonds. For example, although acid and base hydrolysis are commonly used to remove silyl ether protecting groups, such conditions are also liable to hydrolyze the desirable inter-monomer ester bonds. Therefore, in some embodiments, mildly acid or mildly base hydrolysis conditions may be appropriate for the removal of the protecting groups from the polymer. In some embodiments, methods for the deprotection of silyl-ether protected hydroxyls are those which do not use acid or base conditions for removal of the protecting group, and which are more conducive to deprotection of the polymers while preserving their backbone ester bonds. Examples of such methods include those which utilize catalytic fluoride under neutral conditions (DiLauro, et al., Journal of Organic Chemistry, 2011 76(18), 7352-7358.). This method will particularly be suitable for the deprotection of the polymers, i.e., removal of TMS or TDBMS, since it will likely preserve the inter-monomer ester bonds. Other examples include use of sulfated SnO$_2$ (Bhure et al. Synthetic Communications 2008, 38(3), 346-353) and Selectflour (Shah, S. T. A., S. Singh, et al. (2009), Journal of Organic Chemistry, 2009, 74(5), 2179-2182) for the removal of silyl ether protecting groups from polymers described herein, without risk of hydrolysis of inter-monomer ester bonds.

In some embodiments of the drug homopolymers and blocked drug homopolymers of the present invention, if desired, the physical form and characteristics of the polymer can be adapted to resemble the properties of other known polymers by polymer formation in the presence of excess amounts, in molar terms, of co-monomers to form a heteropolymer. In some embodiments, in addition to the drug moiety, the polymer also includes one or more co-monomers. In some embodiments, the co-monomer is covalently bonded to the carboxylic acid group of one drug moiety and the hydroxyl group of a second drug moiety. In some embodiments, the co-monomers are selected so as to modify the properties of the drug release polymer in a desired manner. Examples of such co-monomers include, but are not limited to, 6-hydroxyhexanoic acid, hydroxyl-polyethyleneglycol-carboxylic acid, lactic acid, glycolic acid and beta-hydroxybutyrate.

Figure 5:
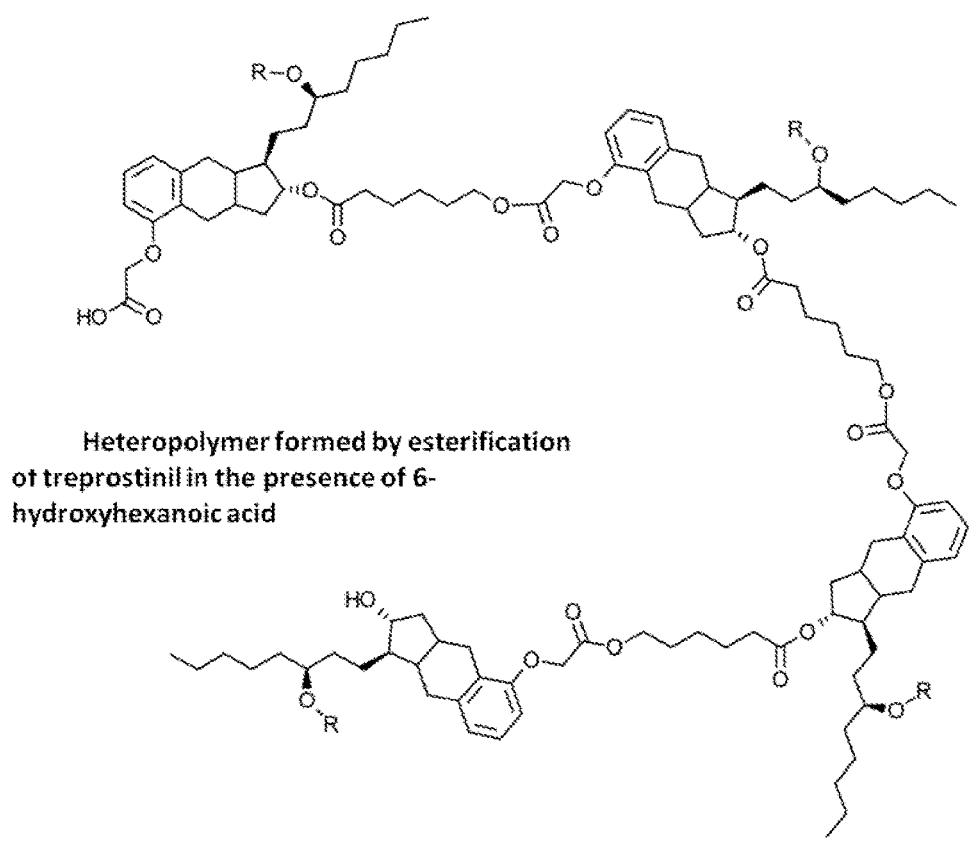
FIG. 5 shows one embodiment of a heteropolymer of treprostinil formed in the presence of 6-hydroxyhexanoic acid as a co-monomer.

In some embodiments, the polymer is designed to adapt to properties of a Polycaprolactone containing composition. For example, FIG. 5 shows a heteropolymer of treprostinil formed in the presence of 6-hydroxyhexanoic acid as a co-monomer. 6-hydroxyhexanoic acid is the open form of caprolactone (a cyclic ester) which is used to form the polymer polycaprolactone using catalyzed ring-opening polymerization method. In one embodiment, the 6-hydroxyhexanoic acid is incorporated as a co-monomer during the Steglich esterification of unblocked treprostinil or blocked treprostinil. Incorporation of a molar excess (e.g., 10×) of the 6-hydroxyhexanoic acid gives rise to a polymer whose predominating characteristic resembles that of polycaprolactone. Polycaprolactone can be melted at 60° C. allowing it to be molded into diverse shapes for drug delivery (e.g., for a solid macro-implant delivered subcutaneously or as a stent). In alternate embodiments, the caprolactone-like heteropolymer (e.g., as depicted in FIG. 5) can be formed from emulsions as a nano- or microparticulate suspension, if required, without recourse to heat-melting, which imposes a finite risk of damaging the drug substance. Other biologically compatible hydroxyl-containing carboxylic acid co-monomers, such as lactic acid and others mentioned herein, would also be suitable for the purpose.

Polycaprolactone solid macro-implants have a longevity of up to three years in vivo and are the basis of several FDA approved products (Woodruff, M. A. and D. W. Hutmacher, Progress in Polymer Science, 2010, 35(10), 1217-1256). Thus, it can be envisaged that the polycaprolactone-like treprostinil heteropolymer (and the poly-lactide-like treprostinil heteropolymer) could be used to achieve a very steady rate of release (achieving classic zero order pharmacokinetics) determined by its surface area. Accordingly, in one embodiment, the polycaprolactone-like treprostinil polymer can be administered as a solid implant. In the case of the polycaprolactone-like drug heteropolymer, much or all of the drug will likely be released in prodrug form as soluble 6-hydroxyhexanoic acid-conjugate prodrug molecules, which would escape the implant site before further hydrolysis to release free drug, thereby avoiding implantation or injection site reactions (e.g., inflammation and pain) due to premature release of free prostacyclin. This feature distinguishes the present technology from previously known compositions in which prostacyclin drugs were embedded non-covalently in polylactide-glycolide (PLGA) sustained release microparticles, as a monthly depot form (Obata et al., American journal of respiratory and critical care medicine, 2008, 177(2), 195-20).

Figure 6:
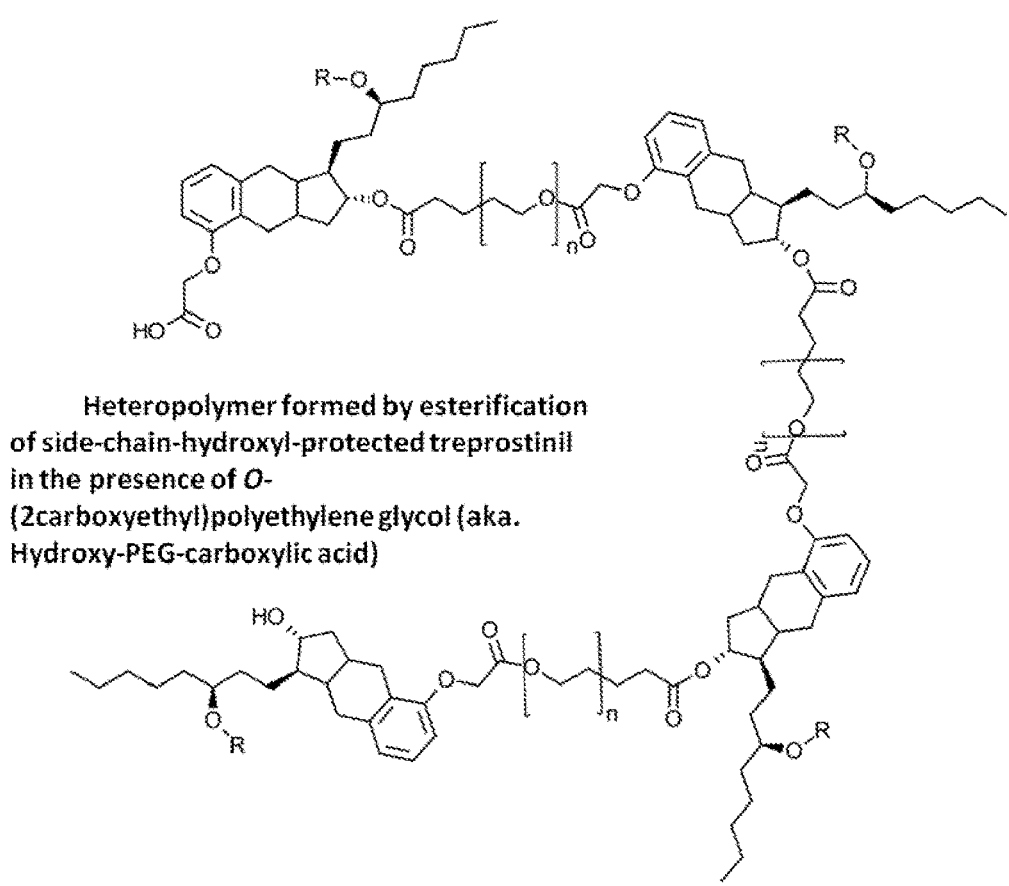
FIG. 6 shows one embodiment of a heteropolymer of treprostinil formed in the presence of a hydroxyl-PEG-carboxylic acid co-monomer.

In some embodiments, the polymer is designed to adapt to properties of a PEG-containing composition, thereby resulting in a water soluble linear polymer. For example, FIG. 6 shows the result of co-polymerization of treprostinil in the presence of a hydroxyl-PEG-carboxylic acid co-monomer. In some embodiments, the PEG co-monomers have an average molecular weight of from about 500 to about 20000, about 800 to about 10000 or about 1000 to about 5000 daltons. In some embodiments, the PEG co-monomers would be in the range of about 1 to about 5 kDa. Use of a molar excess (10x-50x) of the PEG moiety will result in a soluble polymer which would form a solution in saline for injection, and which would dissipate from the injection site before release of significant quantities of free drug that might cause injection site pain reactions. This is because, in the case of the present prostacyclin-PEG heteropolymer, ester bonds need to be cleaved at both ends of the treprostinil moiety in order for drug release to occur. Therefore, the rate of release will be an accelerating function of the molar abundance of 'ends' which increases with time after successive hydrolysis events.

The PEG-heteropolymer can be administered using suitable methods discussed herein. In some embodiments, the PEG-heteropolymer would be most amenable to be administered as a subcutaneous injection, with the aim of avoiding injection-site reactions and achieving 'accelerating release' in the bloodstream to counteract the exponential decay of the drug-polymer conjugate in circulation. The drug release heteropolymers so formed can have an average molecular weight of from about 10,000 to about 200,000 daltons. In some embodiments, the PEG heteropolymers have an average molecular weight of from about 15,000 to 150,000, about 20,000 to 100,000, about 25,000 to 75,000, from about 30,000 to 50,000.

Other polymers, such as monomethoxy-PEG-OH or monomethoxy-PEG-COOH can be used as chain termini individually or collectively, as well as chain terminating reagents. Such polymers, when used in chain termination, can be added in excess after a timed interval of reaction progress. In this manner it will be possible to achieve polymers with narrow dispersity i.e. DM in the range 1.01-1.1. Incorporation of these PEG moieties depends on their relative concentration in the reaction mixture and can impart solubility to the resulting polymer. When used as chain termini, the PEG moieties have a suitable average molecular weight in the range of about 5,000 to about 100,000 daltons, about 10,000 to about 60,000 daltons, about 20,000 to about 40,000 daltons, or about 25,000 to about 30,000 daltons. For example, the use of a monomethoxy-PEG-OH in the Steglich esterification would result in a drug homopolymer with a PEG on the carboxylate end of the polymer. Analogous use of a monomethoxy-PEG-COOH would result in a drug homopolymer with a PEG on the other end. These polymers are different from the polymers based on mono-hydroxy-PEG-carboxylate, wherein the drug monomers are interspersed among the PEG monomers. Di-hydroxy PEG forms (i.e., having a hydroxyl group at both ends of a linker PEG chain) can analogously be subjected to Steglich esterification reactions along with prostacyclin drug molecules having protected or unprotected groups. This would produce symmetrical polymer structures in which the PEG is located centrally, and flanked by homopolymers of the drug moiety either side, oriented in the 'carboxylate-in' orientation as described below:

The PEG-prostacyclin polymers prepared by these methods will have unusually high drug loading capabilities compared to multi-arm PEGs which have a maximum loading capacity of one drug molecule per arm (e.g., 4). No such limit applies to these polymer forms.

The polymers prepared using the methods described herein can be suitably characterized by methods known in the art. The detailed physicochemical properties of the drug release polymers disclosed herein, e.g., solubility, rates of hydrolysis in vivo, can be experimentally determined. By characterizing the physical and chemical properties of the various polymers of the present technology, suitable qualities can be selected for a given drug delivery method, e.g., for subcutaneous administration, for incorporation into stents, etc. Further, for solid dosage forms, the rate of drug release can be controlled by manipulating the surface area of the drug-polymer solid. For example, in various embodiments, the drug release polymers can be designed to be in a nanoparticle, microparticle or macro form. For a given mass of drug release polymer, the rate of release of the drug will be maximal when it is made in nanoparticle form (e.g., 1 nm to 999 nm diameter). In microparticle form (e.g., 10 μm diameter) it will be at least an order of magnitude slower, and in macro-implant form (e.g., as a mesh, sheet or cylinder), it will be slower still. In macro form, the release kinetic can be manipulated by choosing the shape of the implant (e.g., a mesh or sheet instead of a cylinder) in order to achieve an optimal surface area matched to the needs of drug release rate. The rate of drug release is generally proportional to the surface area of the implant and independent of the mass of the implant. For the drug release polymers disclosed herein, the rate of drug release in these macro implementations is determined predominantly by the surface area, and not by the rate of aqueous or enzymatic hydrolysis of the ester bonds. Conversely, conventional drug polymer reversible conjugates, the intrinsic rate of bond hydrolysis, which determines release rate, can be adjusted only in a quantal manner by changing the chemical composition of the polymer-drug conjugate, namely the drug-linker element. The present drug release polymers are, therefore, more adjustable.

Unlike continuous infusion, the drug release polymer of the present technology may be administered conveniently in a small volume by bolus injection of a dose lasting one or more days. In alternative embodiments, it may be made as an implant with duration of action up to three years, with no risk of potentially dangerous bolus release of drug. This approach avoids concerns over the toxicity of polymers, such as PEG in chronic high dosage use, but is also amenable to use with PEG and similar polymers where appropriate. It allows much higher loading in terms of moles of drug per mole of polymer than can be achieved with existing polymer systems. The drug polymer of the present technology is, in one aspect, a polyester, although it is designed to be biodegradable and resorbable by the body and can be manufactured under mild conditions conducive to stability of the monomeric drug molecules and their polymerized moieties.

The physical properties of the polymer differ from that of the parent drug molecule which is water soluble. This is because the major hydrogen bonding elements, i.e., the hydroxyl groups, are engaged in covalent ester bonds and as such, the drug release polymer is likely to be less water soluble than the parent drug molecule. In some embodiments, if rendered in nanoparticulate or microparticulate form, the drug release polymer will be suitable for subcutaneous injection. In other embodiments, in nanoparticulate form, it will also be suitable for intravenous injection. Following injection, the drug undergoes a slow spontaneous hydrolysis by water molecules in the body which accelerates as more bonds are broken. Because cleavage into monomeric forms is not required for solubility, soluble oligomers will escape the injection site at the site of injection sparing injection site pain and inflammatory reactions. Due to the higher reactivity of the ring hydroxyl, it is anticipated that most of the bonds in the polyester homopolymer will involve the ring hydroxyl as opposed to the chain hydroxyl group.

In another aspect, a pharmaceutical composition comprising any of the drug release polymers described herein is provided. In some embodiments, the composition may include a pharmaceutically acceptable excipient. Pharmaceutically acceptable excipients are non-toxic, aid administration, and do not adversely affect the therapeutic benefit of the compound of this invention. Such excipients may be any solid, liquid, semi-solid or, in the case of an aerosol composition, a gaseous excipient that is generally available to one of skill in the art. Pharmaceutical compositions in accordance with the invention are prepared by conventional means using methods known in the art.

The drug release polymer is such that the monomeric prostacylin molecular moieties form the entirety of the backbone of the polymer (in the case of a drug homopolymer of the present invention) or an integral part of the backbone of the polymer (in the case of a heteropolymer of the present invention). In both instances (homopolymer or heteropolymer), except for the two terminal drug moieties of the polymer (i.e. those moieties comprising respectively the carboxylate terminal and the hydroxyl terminal), the drug moieties of the polymer are tethered into the polymer by covalent ester bonds at both ends of the drug molecule moiety, as distinct from being pendant moieties on the end of a polymer chain. By arranging the drug molecules in this way in the structure of the polymer (i.e. tethered at both ends to the polymer and comprising all or part of the polymer backbone, as distinct from 'pendant' at the termini of a carrier polymer such as PEG), several hydrolytic ester bond cleavage events are usually required before a single drug molecule is released. This is because a single cleavage event in a polymer chain gives rise (in the great majority of instances) to two smaller (daughter) polymer chains and not to any free drug molecule, except in the statistically improbable event where the cleavage is at the terminal ester bond joining the first or last drug monomer to the polymeric chain. The longer the chain, the more improbable it becomes that a hydrolytic cleavage event will take place at the ester bond tethering the terminal drug moiety molecular unit, such that the rate of drug release from the polymer can be controlled by manipulating the molecular weight of the polymer which determines its length. This argument for delayed release of drug assumes, to some degree, that the rate of hydrolysis will be the same for the ester bonds at the extreme ends of the polymer as for internal bonds. For soluble polymers, such as co-polymers of the present invention of a prostacyclin with a PEG co-monomer, this arrangement is ensured by the extremely well-hydrated and random-coil properties of PEG which will dominate the properties of the heteropolymer. (In contrast, for insoluble polymers of the present invention, such as drug homopolymers or heteropolymers made with 6-hydroxyhexanoic acid, being less solvated than PEG-prostacyclin heteropolymers, the 'fully hydrated' arrangement of the PEG-prostacyclin heteropolymer will not obtain and surface area of solvent exposure to extracellular fluids of the subcutaneous space, or other body compartment and fluid, will be the determining factor in rates of hydrolysis and drug release). The hydrolytic behaviour of a soluble polymer of the present invention such as the PEG-prostacyclin heteropolymer and the probabilistic nature of its hydrolysis favouring release of pharmacologically inert fragments in the first instance can best be conceived by reference to FIG. 7.

Figure 7:
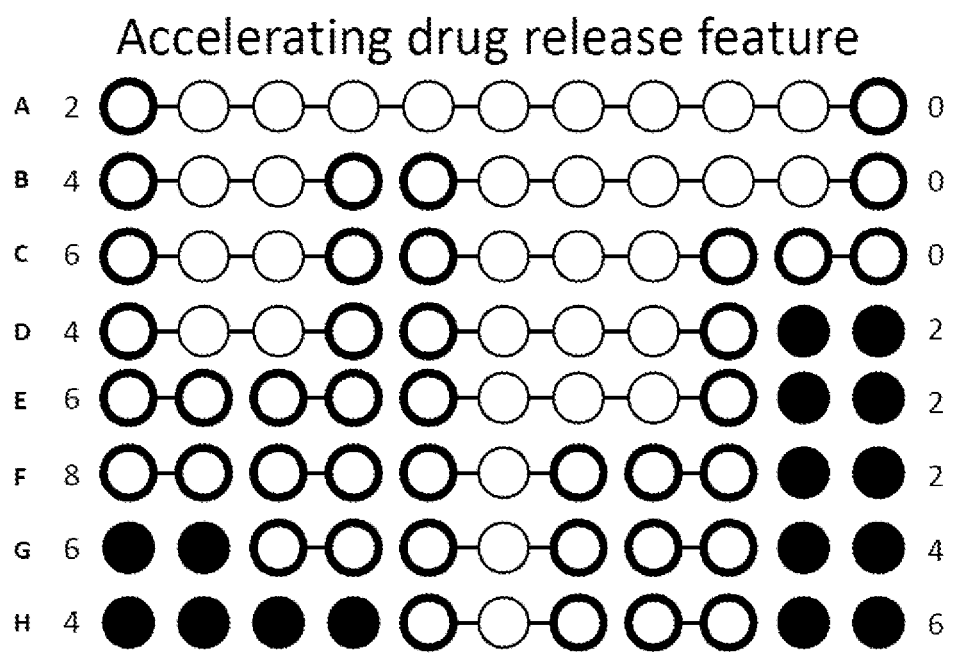
FIG. 7 shows the hydrolytic behavior of a soluble polymer of the present invention having 11 monomeric units (circles) and 10 inter-monomer bonds (A), at time zero (A) and at linear time intervals (B-H).

Shown in FIG. 7 is a drug homopolymer of the present invention having 11 monomeric units (circles) and 10 inter-monomer bonds (A), at time zero (A) and at linear time intervals (B-H) after exposure to an aqueous environment, such as the extracellular fluid following a subcutaneous injection, whereupon a stochastic process of aqueous hydrolysis will ensue. Numbers to the right indicate number of free drug molecules; numbers to the left indicate number of ends. Initially (A) at time zero, there are only two monomeric moieties in the polymer that can give rise to free drug following a single hydrolytic aqueous hydrolysis event (a 'cut'). These are the end moieties (bold circles). The probability that a first cut will give rise to free drug is low therefore (⅕ in the instance of a short polymer such as 'A'. Following the first cut, which most likely (therefore) takes place at an internal bond, the abundance of end groups capable of giving rise to free drug upon a new cut, has doubled (B), as has the probability that a new cut will give rise to free drug. However, the probability that a new cut will occur at an internal bond is still higher than the probability that a cut will take place at an end bond. Following the next cut, the products are 'C', but still (in this particular stochastic instance) there is no free drug released. However, now the abundance of ends with the capability to give rise to free drug following a further cut has increased, such that the next cut gives rise to D, wherein there are two molecules of free drug released. The initial hydrolytic events (i.e. the first two cuts) comprise a lag' phase wherein no free drug is released.

Further cuts may give rise either to free drug or to daughter fragments that are pharmacologically inactive. Eventually the abundance of ends decreases resulting in a decline in the instantaneous rate of drug release approaching a plateau in cumulative drug release over time. The 'accelerating' property of drug release from polymers of this type is more evident when one considers longer polymers. For example, for a polymer of n=101 monomers, the probability of an initial cleavage event giving rise to free drug is $1/50$, such that the lag phase in release of free drug from such a polymer is longer, per unit mass of polymer, than is the case for shorter polymers such as 'A' which have a greater abundance of ends (expressed as ends per unit mass of polymer, or per mole of monomer). For such larger polymer, probabilistically speaking, several cleavage events are required before any free drug is released. As the hydrolysis of the polymer proceeds, the rate of drug release will accelerate. The behaviour of the drug homopolymer may be contrasted to that of pendant polymer constructs (as described in the Ascendis patents cited earlier) wherein there is a fixed rate of drug release, and every cleavage event gives rise to liberation of a free drug molecule. The principle of accelerating drug release (with an initial lag phase) will apply to soluble forms of the polymers of the present invention, particularly those made as heteropolymers with PEG moieties as co-monomers.

This 'lag' in the generation of free drug (though not absolute) has two important effects. First, it allows the drug-polymer to escape the injection site (in the case of a PEG-prostacyclin polymer) before free drug is released. Secondly, as the concentration of polymer in the bloodstream declines, so its rate of drug liberation increases. These factors act firstly to avoid local injection site reaction, due to the action of free drug at the injection site, and secondly to counteract the exponential decline in drug concentration that would normally follow a the administration of a conventional drug-covalent-release polymer. By preventing, substantially, the initiation of drug release at the injection site, the pain, inflammation or other adverse reactions at the administration site can be prevented or reduced. The inert polymer fragments must first reach the bloodstream before they can begin to release drug to a significant extent, adequate to elicit the desired effects of the drug.

The drug release polymers and their pharmaceutical compositions can be formulated for different routes of administration. These include, but are not limited to, oral, transdermal, intravenous, intraarterial, pulmonary, rectal, nasal, vaginal, lingual, inhalation, injection or infusion, including intradermal, subcutaneous, intramuscular, intravenous, intraosseous, and intraperitoneal. Other sustained release dosage forms may include, for example, in depot, an implant, a stent or a transdermal patch form. In some embodiments, the pharmaceutical composition is administered as an injection, e.g., subcutaneous or intramuscular injection. In other embodiments, the pharmaceutical composition is administered as an implant. Various dosage forms may be prepared using methods that are standard in the art (see e.g., Remington's Pharmaceutical Sciences, 16th ed., A. Oslo editor, Easton Pa. 1980).

In another embodiment, a reconstituted or liquid pharmaceutical composition comprising the drug release polymer is administered via a first method of administration and a second reconstituted or liquid pharmaceutical composition comprising drug release polymer is administered via a second method of administration, either simultaneously or consecutively. Said first and second method of administration can be any combination of topical, enteral administration, parenteral administration, inhalation, injection, or infusion, intraarticular, intradermal, subcutaneous, intramuscular, intravenous, intraosseous, and intraperitoneal, intrathecal, intracapsular, intraorbital, intracardiac, transtracheal, subcuticular, intraarticular, subcapsular, subarachnoid, intraspinal, intraventricular or intrasternal administration.

In some embodiments, the polymer is administered as an injection. Unlike the free drug molecule, the drug release polymers of the present technology can be injected without causing injection site pain, since they diffuse from the injection site, in prodrug-oligomeric form, entering the blood and lymphatic systems, before release of free drug by further aqueous hydrolysis. In some embodiments, the polymer is administered via inhalation. In other embodiments, the polymer is administered orally. Upon inhaled or oral administration, the oligomeric forms would undergo a gradual sustained release of free drug avoiding the dose-limiting 'spike' or 'peak' in blood concentration that generally ensues following oral or inhaled delivery of free drug.

Unlike continuous infusion in conventional controlled release formulations, the drug release polymer of the present technology may be administered conveniently in a small volume by bolus injection of a dose lasting one or more days. In alternative embodiments, it may be made as an implant with duration of action up to three years, with no risk of potentially dangerous bolus release of drug. This approach avoids concerns over the toxicity of polymers, such as PEG in chronic high dosage use, but is also amenable to use with PEG and similar polymers where appropriate. It allows much higher loading in terms of moles of drug per mole of polymer than can be achieved with existing polymer systems. The drug polymer of the present technology is, in one aspect, a polyester, although it is designed to be biodegradable and resorbable by the body and can be manufactured under mild conditions conducive to stability of the monomeric drug molecules and their polymerized moieties.

In some embodiments, the drug release polymers of the present technology can be administered as a subcutaneous injection or to inhaled delivery. In other embodiments, where needed, the polymer, in a nanoparticle or soluble form, can be administered intravenously. In yet another embodiment, being a polyester, the polymer can be administered could be used in the formation or coating of plastic stents for slow sustained release of drug at suitable anatomical sites (e.g., within the arterial vessels of the pulmonary circulation) effecting localized drug delivery to the target tissue (e.g., in the case of pulmonary hypertension) while sparing systemic side effects. Such stents are known in the art, for example bioresorbable coronary stents for the sustained release of anti-proliferative drugs such as paclitaxel and everoliumus, to prevent restenosis after balloon angioplasty, and have recently been reviewed by Ormiston, J. A. and P. W. Serruys, Circulation. Cardiovascular interventions, 2009, 2(3), 255-260. The first example of the use of a bioabsorbable (bioresorbable) stent in humans used polylactic acid (a polyester), which was pioneered by Tamai and colleagues (Onuma, Y., S. Garg, et al., EuroIntervention journal of EuroPCR in collaboration with the Working Group on Interventional Cardiology of the European Society of Cardiology 5 Suppl F: F109-111, 2009). Analogously, according to the rationale of the present technology, techniques for the formation of polylactide (polylactic acid, PLA) and polylactide-glycolide (PLGA) could be used for the covalent incorporation of a pro-inflammatory drugs such as prostacyclins, e.g., treprostinil, iloprost, cicaprost and beraprost. Covalent incorporation, as part of a homopolymer or heteropolymer, allows desorption of the drug from the site as a transient covalent prodrug form, which may then be hydrolyzed to the active form during circulation.

Depot arrangements, such as stents, can also be utilized to administer drugs which have very short pharmacokinetics for conventional modes of drug administration and delivery (e.g., intravenous) due to their inherent chemical instability. Such drugs include, e.g., natural prostacyclin molecule, i.e., prostaglandin-I2. These drugs, when utilized as the drug release polymer of the present technology, can be released locally into the pulmonary arterial circulation and will have a lesser availability in the general circulation outside of the pulmonary system, thereby avoiding systemic side effects and allowing higher doses to be administered locally to the affected vascular (arterial) tissues of the lung to achieve a more favorable therapeutic ratio.

Administration by subcutaneous injection is most suitable for soluble forms of the drug release polymer, such as the linear PEG-prostacyclin co-polymer. In some embodiments, a vial of polymer solution can be lyophilized from water or dried from solvent by evaporation under vacuum. The dry drug release polymer can then be reconstituted just before use as a solution or suspension in a medium suitable for subcutaneous injection. Such mediums include, e.g., phosphate-buffered physiological saline of pH, or buffers such as succinate, or citrate could be used to administer saline solutions buffered at pH's more conducive to polymer stability, e.g., pH 6.0. For subcutaneous injection, suitable polymer lengths can include chain lengths from about $n=2$ up to about $n=100$, about $n=10$ up to about $n=100$, about $n=15$ up to about $n=80$, about $n=20$ up to about $n=70$ or about $n=25$ up to about $n=50$.

For inhaled administration, the polymer is, in one embodiment, at least a homodimer (for administration in liquid aerosol form). For inhaled administration, suitable polymer lengths can include chain lengths from about $n=25$ up to about $n=200$, about $n=50$ up to about $n=150$ about $n=60$ up to about $n=100$, or about $n=70$ up to about $n=90$. In some embodiments, the polymer length is $n=50$ or greater. In some embodiments, the polymer has sufficient length and particle size so that it can be administered as a solid form in a metered dose dry powder inhaler. For example, the drug release polymer can have particles having mean or median size of about 3 micrometers, favoring deposition in the alveoli of the lung for optimal access to pulmonary arterioles. Low oligomer forms (such as a dimer or a trimer) would be less amenable to uptake than the monomer drug molecule such that lung administration of polymer forms would form a local depot which would gradually elute free drug from the alveoli into the pulmonary arterioles. In contrast to non-polymerized, free drug, which is soluble and rapidly escapes the lung tissue into the general circulation where it causes systemic side-effects, the polymeric forms of drug (dimer, trimer and polymers) would be 'captive' in the alveoli, forming a local, inert, sustained release reservoir. Further, because the present polymers need to undergo hydrolysis before absorption can occur, they avoid the spike in blood concentration that occurs immediately following inhalation of non-polymerized drugs, thereby avoiding the dose limiting side effects associated with inhaled drug formulations. Moreover, the polymeric formulations provide a more constant level of free drug in the vicinity of the pulmonary arterioles than the inhaled forms of free drugs.

Polymers and compositions described herein maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

The present technology is different in a number of respects from conventional drug release solutions known in the art. Firstly, many sustained release strategies are known to use covalent ester bonds. In the present technology, the bond is not to a polymer carrier (as in classical drug-polymer covalent release conjugates) or to a substituent group (as in classical prodrug strategies for non-polymer drugs), but rather to another molecule of the drug itself. As such, it eliminates concerns about the toxicology of the polymer or substituent element, since the polymer dissolves, upon aqueous hydrolysis, to release only the drug, such that the chemical toxicology of the new polymer is virtually identical to that of the parent drug molecule, which generally is known. Further, the cleavage of the drug release polymers of the present technology does not inevitably result in release of free drug. This is because, initially, random cleavage of the new polymer results predominantly in the release of polymer fragments which are, as yet, inactive. Therefore, premature cleavage of the polymer, e.g., upon storage, before administration, does not give rise to significant amounts of free drug that might lead to contamination and adverse reactions, e.g., causing injection site reaction in case of an injectable formulation.

Compared to classical polymer prodrug strategies, the present drug release polymers exhibit flexibility in control of drug release properties. Unlike a conventional covalent polymer release strategy, wherein the rate of release of the drug is dictated by the fixed rate of hydrolysis of the bond attaching the drug to the polymer (e.g., an ester bonded PEG-drug prodrug conjugate), for the drug release polymer of the present technology, the rate of release of free drug is a complex function of the rate of ester bond hydrolysis and the length of the polymer. The drug release polymers which have shorter lengths and have a greater abundance of ends per unit mass will give rise to more rapid liberation of free drug. On the other hand, drug release polymers with longer lengths will result in slower release of free drug, such that drug release rates can be controlled by controlling the length or average length of the drug during polymer synthesis. As such, the rate of release of the drug for such a polymer is more of an analog function less restricted by the quantal variation between different chemistries of attachment and can be 'tuned' to maximum effect. In embodiments where the polymer is administered in the insoluble 'implant' or 'stent' forms, as exemplified by the heteropolymer with 6-hydroxyhexanoic acid, the rate of drug release can be controlled by manipulating the surface area of the implant or the stent.

In some embodiments, only cleavage of the end bonds gives rise to active product. As successive cleavages occur randomly along the length of the polymer, the concentration of ends increases exponentially, and so too does the probability that a new random cleavage will occur at an end, i.e., the rate of drug release is proportional to the abundance of 'ends.' Depending upon the length, the polymer would be insoluble or soluble in aqueous solutions. In some embodiments, where the drug release polymer is insoluble, it can be administered as a local depot (subcutaneous or by dry powder inhalation), or incorporated into stents. Shorter polymer chain lengths, e.g., dimmers and trimers, would likely result in soluble forms. The rate of active drug release is more likely to be 'analog' in character and could be tuned by adjustment of polymer length. This is advantageous for avoiding adverse reactions, for example, to avoid the spike in blood concentration following inhalation, possibly avoiding dose limiting systemic side effects.

In yet another aspect, a method of diagnosing, treating, controlling, delaying or preventing in a mammalian patient, e.g., in a human, in need of the treatment of one or more conditions, diseases or disorders comprising administering to said patient a therapeutically effective amount of a drug release polymer of the present technology or a pharmaceutical composition comprising the drug release polymer or a pharmaceutically acceptable salt thereof, is provided. It will be understood that the conditions, diseases or disorders will depend on the drug moiety which is being polymerized and its therapeutic activity. For example, if the drug moiety has anti-cancer activity, it will be administered to a cancer patient; if the drug moiety has an anti-inflammatory activity, it will be administered to a patient who suffers from an inflammatory disease, like rheumatoid arthritis, inflammatory bowel disease or Crohn's disease; a drug moiety which has neurological activity will be administered to a patient suffering from a neurological disease like Alzheimer's disease or Parkinson's disease, and so on and so forth.

Exemplary conditions, diseases or disorders that can be prevented and/or treated with the drug release polymer of the present technology include, but are not limited to, pulmonary hypertension, ischemic diseases (e.g., peripheral vascular disease including peripheral arterial disease, Raynaud's phenomenon including Raynaud's disease and Raynaud's syndrome, scleroderma including systemic sclerosis, myocardial ischemia, ischemic stroke, renal insufficiency), ischemic ulcers including digital ulcers, heart failure (including congestive heart failure), portopulmonary hypertension, interstitial lung disease, idiopathic pulmonary fibrosis, conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation. In one embodiment, the present technology relates to a treprostinil controlled release polymer or a pharmaceutically acceptable salt thereof or a pharmaceutical composition thereof for use in a method of treating or preventing a disease or disorder which can be treated and/or prevented by treprostinil. In one embodiment, the disease or disorder is pulmonary arterial hypertension. Non-small-cell lung cancer is another indication to which the present invention is applicable, wherein treprostinil (or other prostacyclin drug such as iloprost) can be used as an agonist of the Wnt signalling pathway, arresting the growth of lung cancer cells and inhibiting new tumour formation (Tennis, M. A., et al., Neoplasia, 2010, 12(3): 244-253.).

The present invention, thus generally described, will be understood more readily by reference to the following examples, which are provided by way of illustration and are not intended to be limiting of the present invention.

EXAMPLES

Example 1. Preparation of Polymer Compound (A)

The polymer forming reaction is achieved most favorably by a modification of the well known Steglich esterification (Höfle, G., W. Steglich, et al. 1978) as here described for the drug homopolymer of FIG. 2. Dissolve 30.5 mg 0.78 mmol of treprostinil in dichloromethane (DCM 25 mL) and deionized $H_2O$ (600 Add dimethylaminopyridine (DMAP 760 mg, 6.24 mmol) and EDC HCl (1.19 g, 6.24 mmol) dissolved in DCM (10 ml). Stir the reaction mixture at room temperature until reaction is complete, or reaches a plateau (as judged by HPLC/MS measuring free treprostinil), i.e. for 4-8 h or for 16 h overnight, at which time no further free treprostinil is being consumed in polymer formation. Add the DCM solution to excess water, while stirring vigorously, and evaporate off the dichloromethane in a rotary evaporator. Recover the particulate polymer by filtration, and wash with water to remove excess EDC and by-products, and any unreacted treprostinil. Further purification can be effected by dissolving the dried polymer in DCM and conducting gel permeation chromatography in DCM according to methods known in the art. The first (broad) peak to elute in such chromatography will be treprostinil polymers, later eluting peaks are residual contaminants and may be discarded.

An alternative method to achieve the drug homopolymer of FIG. 2 is to apply the esterification method of Sharghi, Babak et al. 1998, as here described. To a mixture of $MeSO_3H$ (1.0 mL, 15 mmol) and $Al_2O_3$ (0.27 g, 3.0 mmol), 2.0 mmol of treprostinil is added. The mixture is stirred and heated in an oil bath at 80° C. for 7-120 min. Then the mixture is poured into water, at which time the polymer precipitates, and is recovered by filtration along with the $Al_2O_3$, and washing with water (to remove free treprostinil). The recovered polymer and $Al_2O_3$ mixture is then resuspended in water and the suspension is extracted twice with ethyl acetate or chloroform (20 mL) to dissolve the polymer leaving behind the alumina. The organic layer is then washed with a saturated solution of sodium bicarbonate (20 mL). Finally, the organic layer is dried over calcium chloride ($CaCl_2$) and evaporated in vacuum to obtain a residue, which is the polymer product.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains All patents, patent applications, publications and references cited herein are incorporated by reference in their entirety to the extent as if they were individually incorporated by reference.

What is claimed is:

1. A method for producing a drug release polymer, comprising esterifying a drug moiety which comprises at least one carboxylic acid group and at least one hydroxyl group in the presence of a coupling agent and a catalyst to form a drug release polymer comprising a plurality of releasable drug moieties, wherein at least some drug moieties are covalently attached to each other via an ester bond formed by a previously present carboxylic acid group of one drug moiety and a previously present hydroxyl group of another drug moiety and wherein the drug moiety is a prostacyclin compound comprising at least one carboxylic acid group and at least one hydroxyl group.

2. The method of claim 1, wherein the coupling agent is N-(3-Dimethylaminopropyl)-N'-ethylcarbodiimide or N,N'-Dicyclohexylcarbodiimide.

3. The method of claim 1, wherein the catalyst is 4-(Dimethylamino)pyridine.

4. The method of claim 1, wherein the drug moiety has at least two carboxylic acid groups and the method further comprises blocking one or more of the carboxylic acid groups of the drug moiety in excess of one carboxylic group, prior to esterification.

5. The method of claim 1, wherein the drug moiety comprises at least two hydroxyl groups and the method further comprises blocking one or more of the hydroxyl groups of the drug moiety in excess of one hydroxyl group, prior to esterification.

6. The method of claim 5, wherein the one or more hydroxyl groups are blocked using trimethylsilyl chloride or t-butyldimethylsilyl chloride.

7. The method of claim 1, wherein the prostacyclin compound is selected from the group consisting of epoprostenol, treprostinil, beraprost, iloprost, cicaprost, and prostaglandin I2.

8. The method of claim 7, wherein the prostacyclin compound is treprostinil.

9. The method of claim 1, wherein the prostacyclin compound is a compound of Formula (I)

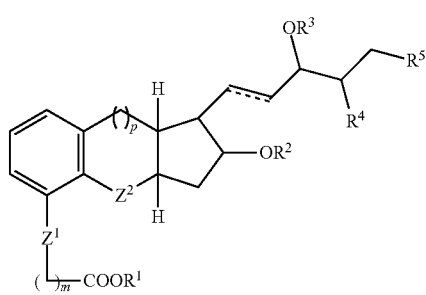

wherein
⫽ represents a single or a double bond;
$Z^1$ and $Z^2$ each independently represents an O or $CH_2$;
p=0 or 1;
m=1, 2, or 3;
$R^1$ represents a H or an acid protective group;
$R^2$ and $R^3$ each independently represents a H or a hydroxyl protective group;
$R^4$ represents H or a $C_{1-6}$ alkyl; and
$R^5$ represents a $C_{1-6}$ alkyl group or $C_{2-8}$ alkynylene group.

10. The method of claim 1, wherein the polymer is at least a trimer.

11. The method of claim 1, wherein the covalent attachment is an ester bond formed between said at least one hydroxyl group and said at least one carboxylic group.

12. The method of claim 1, wherein the polymer further comprises a co-monomer covalently bonded to the carboxylic acid group of one drug moiety and the hydroxyl group of a second drug moiety.

13. The method of claim 12, wherein the polymer is insoluble in water.

14. The method of claim 12, wherein the polymer is soluble in water.

15. The method of claim 12, wherein the co-monomer is selected from the group consisting of 6-hydroxyhexanoic acid, beta-hydroxybutyric acid, hydroxyl-polyethylene glycol-carboxylic acid, lactic acid, and glycolic acid.

16. The method of claim 1, wherein the drug moieties that form the polymer have a structure selected from the group consisting of Formulae (IIa), (IIb), and (IIc):

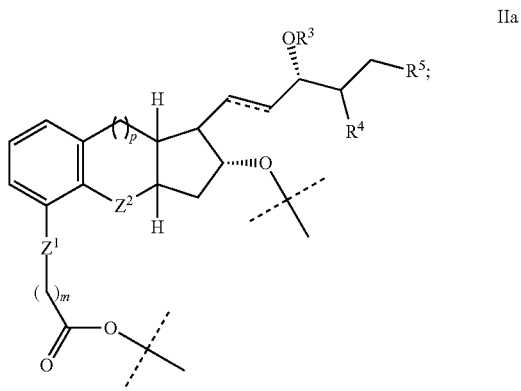

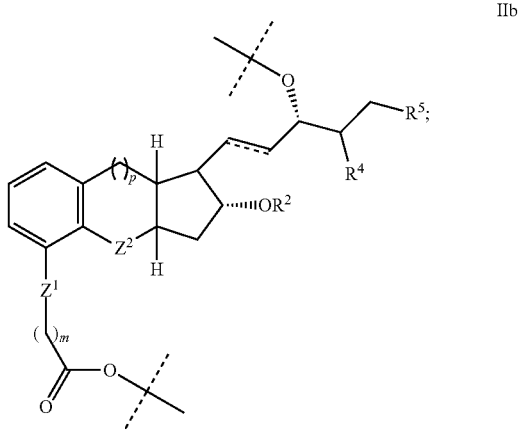

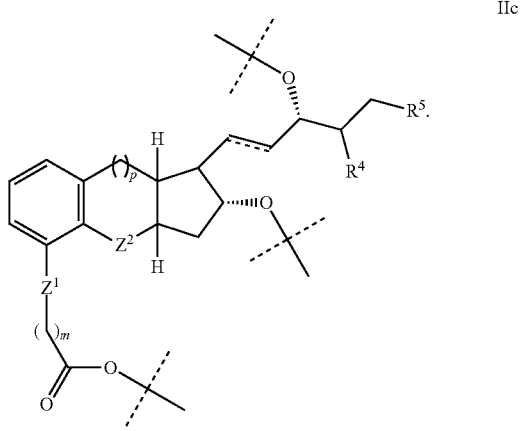

* * * * *

UNITED STATES PATENT AND TRADEMARK OFFICE
CERTIFICATE OF CORRECTION

| | |
|---|---|
| PATENT NO. | : 10,494,327 B2 |
| APPLICATION NO. | : 15/698852 |
| DATED | : December 3, 2019 |
| INVENTOR(S) | : Peter Laing |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 24 days.

Signed and Sealed this
Tenth Day of January, 2023

Katherine Kelly Vidal
*Director of the United States Patent and Trademark Office*